(12) United States Patent
Delisle et al.

(10) Patent No.: US 10,201,714 B2
(45) Date of Patent: Feb. 12, 2019

(54) ADVANCED WARNING INDICATOR FOR EMERGENCY MEDICAL DEVICES

(71) Applicant: KONINKLIJKE PHILIPS N.V., Eindhoven (NL)

(72) Inventors: Norman Maurice Delisle, Manchester, MA (US); David K Hunt, Nashua, NH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/540,119

(22) PCT Filed: Dec. 24, 2015

(86) PCT No.: PCT/IB2015/059983
§ 371 (c)(1),
(2) Date: Jun. 27, 2017

(87) PCT Pub. No.: WO2016/108163
PCT Pub. Date: Jul. 7, 2016

(65) Prior Publication Data
US 2018/0001097 A1 Jan. 4, 2018

Related U.S. Application Data

(60) Provisional application No. 62/097,763, filed on Dec. 30, 2014.

(51) Int. Cl.
*A61N 1/39* (2006.01)
*G06F 19/00* (2018.01)
(Continued)

(52) U.S. Cl.
CPC .......... *A61N 1/3925* (2013.01); *A61N 1/39* (2013.01); *A61N 1/3904* (2017.08);
(Continued)

(58) Field of Classification Search
None
See application file for complete search history.

(56) References Cited

U.S. PATENT DOCUMENTS 5,899,925 A * 5/1999 Ochs ................... A61N 1/3931
607/5
7,277,752 B2 * 10/2007 Matos ................. A61B 5/0006
607/5
(Continued)

FOREIGN PATENT DOCUMENTS

WO 2015145272 A1 10/2015

*Primary Examiner* — Brian T Gedeon (57) ABSTRACT

An emergency medical device (20) (e.g., an external defibrillator/monitor) employing an emergency medical subsystem (21) for executing an emergency medical procedure (e.g., a monitoring subsystem (21) and a therapy subsystem (21)), and an emergency medical controller (23) for controlling an activation of the emergency medical subsystem (21). The subsystem (21) includes one or more operational components (22). In operation, the controller (23) conditionally actuates a device readiness indicator (24) (e.g., auditory or visual) indicative of an operational readiness of the operational component(s) (22), and conditionally actuates a failure warning indicator (25) (e.g., auditory or visual) indicative of a pending failure of the operational readiness of the operational component(s) (22). The failure warning indicator (25) may be actuated based on a predictive failure analysis of a premature degradation of the operational component(s) (22), a repeated occurrence of error conditions of the operational component(s) (22) (particularly recoverable error conditions), and a shortened reliable life of the operational component(s) (22).

21 Claims, 3 Drawing Sheets

(51) Int. Cl.
  *G16H 40/40* (2018.01)
  *G16H 40/63* (2018.01)
  *G01R 31/28* (2006.01)

(52) U.S. Cl.
  CPC ............ *A61N 1/3993* (2013.01); *G06F 19/00* (2013.01); *G16H 40/40* (2018.01); *A61B 2560/0276* (2013.01); *G01R 31/2836* (2013.01); *G16H 40/63* (2018.01)

(56) References Cited

U.S. PATENT DOCUMENTS

| | | | |
|---|---|---|---|
| 7,510,526 B2* | 3/2009 | Merry | A61N 1/39 600/300 |
| 7,570,994 B2* | 8/2009 | Tamura | A61N 1/3975 607/5 |
| 7,729,757 B2* | 6/2010 | Parascandola | G09B 23/288 607/2 |
| 8,165,849 B2 | 4/2012 | Mannar et al. | |
| 8,344,899 B2* | 1/2013 | Sullivan | G08B 3/10 340/384.1 |
| 8,985,326 B2* | 3/2015 | Halsne | A61N 1/3968 206/363 |
| 9,289,621 B2* | 3/2016 | Aoyama | A61N 1/3975 |
| 9,808,639 B2* | 11/2017 | Delisle | A61N 1/3968 |
| 2004/0143297 A1* | 7/2004 | Ramsey, III | A61N 1/3975 607/5 |
| 2011/0190839 A1 | 8/2011 | Vaisnys et al. | |
| 2013/0304146 A1* | 11/2013 | Aoyama | A61N 1/3975 607/6 |
| 2013/0317560 A1 | 11/2013 | Barnes et al. | |
| 2015/0265844 A1 | 9/2015 | Powers | |
| 2015/0321020 A1 | 11/2015 | Gumbrell | |

* cited by examiner

ADVANCED WARNING INDICATOR FOR EMERGENCY MEDICAL DEVICES

This application is a national stage application under 35 U.S.C. § 371 of International Application No. PCT/IB2015/059983 filed on Dec. 24, 2015 and published in the English language on Jul. 7, 2016 as International Publication No. WO 2016/108163, which claims priority to U.S. Patent Application No. 62/097,763 filed on Dec. 30, 2014, the entire disclosures of which are incorporated herein by reference.

FIELD OF THE INVENTION

The present invention generally relates to emergency medical devices (e.g., an external defibrillator/monitor). The present invention specifically relates to an advanced warning of a pending failure of an operationally ready emergency medical device.

BACKGROUND OF THE INVENTION

An emergency medical device (e.g., an external defibrillator/monitor) is used in emergency lifesaving situations where seconds count. For example, when someone succumbs to a sudden cardiac arrest, the likelihood of resuscitation decreases each minute thereafter. Thus, it is critically important for the emergency medical device to be ready for use when it is needed. Consequently, device readiness indicators are commonly used in emergency medical devices to inform the user whether or not the emergency medical device is ready-for-use.

In practice, many emergency medical devices are turned-off most of the time and standard protocol mandates a periodic assessment of whether the emergency medical device is ready-for-use. To this end, an emergency medical device typically performs automatic self-tests on an hourly or daily basis when the emergency medical device is turned off, but has power available to conduct the self-tests. The device readiness indicator provides visual and/or auditory signals informative of either a pass result or a fail result of the self-tests. For example, the device readiness indicator may be displayed as a green check mark icon to indicate a ready-for-use pass result or as a red X mark to indicate a not-ready-for-use failed result.

A limitation of this scheme is that there is no advanced warning of a pending failure of a ready-for-use emergency medical device. Specifically, the device readiness indicator will indicate the emergency medical device is ready-for-use until self-tests indicate the emergency medical device is no longer ready-for-use. Working with only this Boolean indicator, designers of emergency medical devices are constrained to characterize marginal test results as failures, with the possible implication of a false failure that needlessly takes a properly functioning emergency medical device out of service. A further consequence of this Boolean indicator is that a subsystem monitoring of the emergency medical device fails to detect condition(s) that indicate the emergency medical device is likely to operationally fail in the near future.

Figure 1:
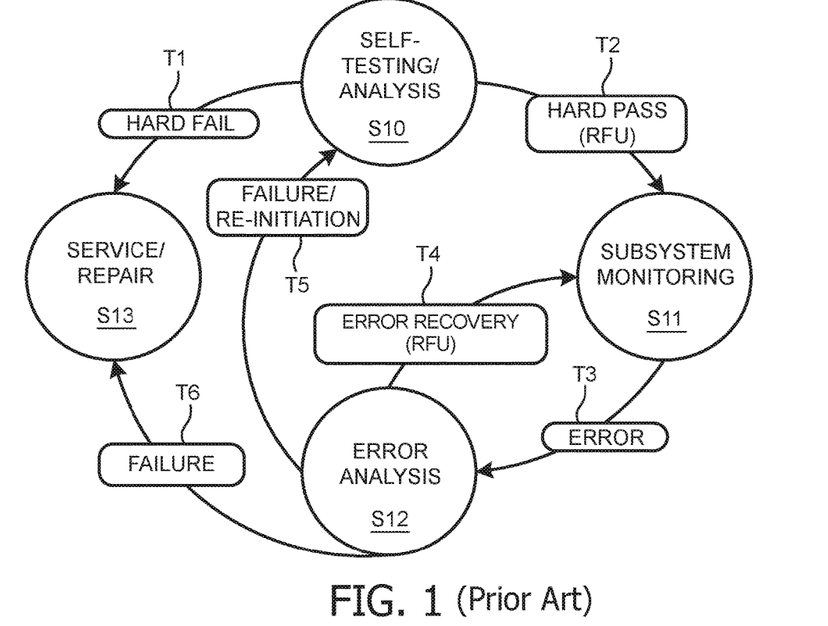
FIG. 1 illustrates an exemplary state diagram to demonstrate an operational readiness assessment method of an emergency medical device as known in the art.

More particularly, referring to FIG. 1, an illustrated operational readiness assessment state diagram consists of a self-testing/analysis state S10, a subsystem monitoring state S11, an error analysis state S12 and a service/repair state S13 for assessing the operational readiness of the emergency medical device.

Self-testing/analysis state S10 involves an execution of various self-testing by the emergency medical device of each subsystem of the emergency medical device. As will be further explained subsequently herein, a subsystem of the emergency medical device employs operational components for executing an emergency medical procedure including, but not limited to, an electrocardiogram monitoring procedure, a defibrillation shock therapy procedure, a synchronized cardioversion therapy procedure and a transcutaneous pacing therapy procedure. The self-testing of such operational components involves a delineation of a hard functional limit between being deemed either operationally ready or inoperable for purposes of the associated emergency medical procedure.

If one or more of the subsystems fails self-test(s) executed by the emergency medical device, then the emergency medical device is triggered to transition T1 to service/repair state S13 whereby the emergency medical device indicates a service/repair is needed for the emergency medical device (e.g., a red X mark icon is activated).

Otherwise, if the subsystem(s) pass the self-tests executed by the emergency medical device, then the emergency medical device is triggered to transition T2 to subsystem monitoring state S11 whereby the emergency medical device indicates all subsystems are ready-for-use ("RFU") (e.g., a green check mark icon is activated).

While waiting for use or actually in use during subsystem monitoring state S11, the emergency medical device will be triggered to transition T3 to error analysis state S12 when an error by a subsystem occurs that threatens the operational readiness of the emergency medical device. The error may be a recoverable error or non-recoverable error (i.e., a failure).

If the emergency medical device is able to recover from an error, then the emergency medical device is triggered to transition T4 back to subsystem monitoring state S11.

If the emergency medical device is unable to recover from an error but is reinitiated nonetheless by an operator or automatically, then emergency medical device is triggered to transition T5 to self-testing/analysis state S10.

If the emergency medical device has failed subsystem(s) without being reinitialized, then the emergency medical device is triggered to transition T6 to service/repair state S13.

In practice, the operational readiness assessment state diagram may be implemented in various modes, but regardless the subject state diagram fails to detect condition(s) that indicate a subsystem of the emergency medical device is likely to operationally fail in the near future.

SUMMARY OF THE INVENTION

The present invention incorporates a predicative failure analysis within the emergency medical device to detect condition(s) indicative of likely operational failure in the near future of operational component(s) of the emergency medical subsystem(s).

One form of the present invention is an emergency medical device (e.g., an external defibrillator/monitor) employing an emergency medical subsystem for executing an emergency medical procedure (e.g., a monitoring subsystem or a therapy subsystem), and an emergency medical controller for controlling an activation of the emergency medical subsystem. The subsystem includes one or more operational components. In operation, the controller conditionally actuates a device readiness indicator (e.g., auditory or visual) indicative of an operational readiness of the operational component(s), and conditionally actuate a failure warning indicator (e.g., auditory or visual) indicative of a pending failure of the operational component(s). The failure warning indicator may be actuated based on a predictive failure analysis of a premature degradation of the operational component(s), a repeated occurrence of error conditions of the operational component(s) (particularly recoverable error conditions), and a shortened reliable life of the operational component(s).

For purposes of the present invention, terms of the art including, but not limited to, "emergency medical device", "emergency medical subsystem", "emergency medical procedure", "operational component" and "device readiness indicator" are to be interpreted as known in the art of the present invention and exemplary described herein.

For purposes of the present invention, the "device readiness indicator" and the "failure warning indicator" may be segregated indicators (e.g., the device readiness indicator being a dedicated visual indicator and the failure warning indicator being displayed on a user interface) or integrated indicators (e.g., the failure warning indicator being a flashing of the dedicated visual indicator).

For purposes of the present invention, the term "controller" broadly encompasses all structural configurations of an application specific main board or an application specific integrated circuit housed within or linked to an emergency medical device for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s).

For purposes of the present invention, the term "application module" broadly encompasses an electronic circuit or an executable program (e.g., executable software and/firmware) for executing a specific application.

A second form of the present invention is a method of operating the emergency medical device. The method involves the emergency medical controller conditionally generating a device readiness indicator indicative of an operational readiness of the operational component(s) to execute an emergency medical procedure, and the emergency medical controller conditionally generating a failure warning indicator indicative of a pending failure of the operational readiness of the operational component(s) to execute the emergency medical procedure.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate an understanding of the present invention, exemplary embodiments of the present invention will be provided herein directed to an implementation of a predictive failure analysis by an emergency medical controller of the present invention.

Figure 2:
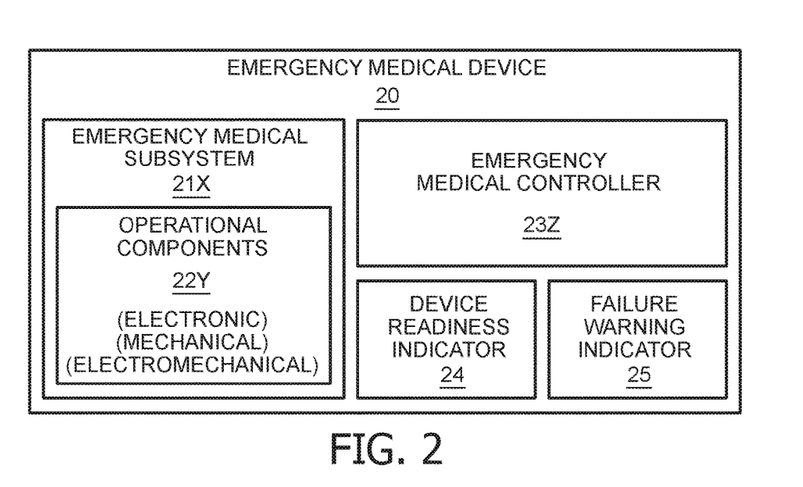
FIG. 2 illustrates an exemplary embodiment of an emergency medical device in accordance with the present invention.

Referring to FIG. 2, an emergency medical device 20 (e.g., an external defibrillator/monitor) employs an X number of emergency medical subsystems 21, X≥1 for executing an X number of emergency medical procedures. Examples of subsystems 21 include, but are not limited to:
(1) an electrocardiogram ("ECG") monitoring subsystem for generating and displaying an ECG of a patient connected via leads to device 20; and
(2) a therapy subsystem for applying a defibrillation shock, a synchronized cardioversion or a transcutaneous pacing to a patient connected/coupled via leads/pads/paddles to device 20.

Each subsystem 21 employs a Y number of operational components structurally assembled to execute the corresponding emergency medical procedure, Y≥1. Examples of operational components 22 include, but are not limited to, electronic components, mechanical components and electromechanical components currently utilized in commercially available emergency medical devices (e.g., Philips HeartStart MRx and XL+defibrillators/monitors).

Figure 3:
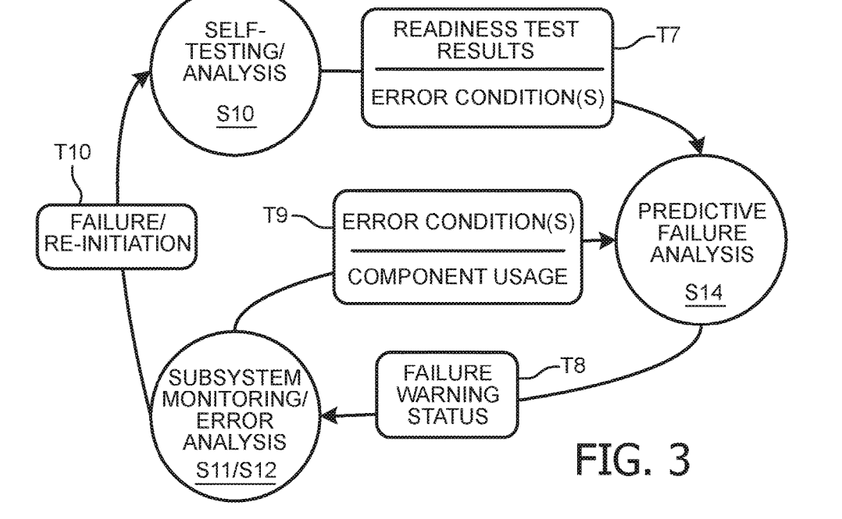
FIG. 3 illustrates an exemplary state diagram to demonstrate the inventive principles of a failure warning method of an emergency medical device in accordance with the present invention.

Emergency medical device 20 further employs a Z number of emergency medical controller 23, Z≥1, for controlling an activation of subsystem(s) 21 in executing the emergency medical procedure(s). In practice, each controller 23 may employ an operating system module as known in the art for overall device control and various application modules for self-testing, predicative failure analyzing and activating subsystem(s) 21. Examples of application modules include, but are not limited to:
(1) an operational readiness testing module for executing self-testing of subsystem(s) 21 and controller 23 as known in the art and previously exemplarily described herein (FIG. 1);
(2) a predictive failure analysis module for detecting condition(s) indicative of likely operational failure in the near future of subsystem(s) 21 and controller 23 as will further exemplarily described herein (FIG. 3);
(3) a monitoring module for controlling an activation of a monitoring subsystem as previously exemplarily described herein (FIGS. 2); and
(4) a therapy module for controlling an activation of a therapy subsystem as previously exemplarily described herein (FIG. 2).

More particular to an operational readiness testing module, a controller 23 actuates a device readiness indicator 24 indicating either:

(1) an operational readiness of operational component(s) 22 of each subsystem 21 based on a pass result of an operational readiness testing performed by the operational readiness testing module; or (2) an inoperable readiness of one or more operational component(s) 22 of one or more subsystems 21 based on a failed result of an operational readiness testing performed by the operational readiness testing module.

In practice, device readiness indicator 24 may have various structures including, but not limited to:

(1) a visible light form (e.g., a green check mark for operational readiness, a red X for inoperable readiness or a flashing light for immediate attention);

(2) an iconic and/or textual visual form (e.g., an icon and/or text displayed on a monitor); and/or (3) an audio form (e.g. a series of beeps for immediate attention or a voice recording stating either operational readiness or inoperable readiness).

More particular to a predictive failure analysis module, a controller 23 actuates a failure warning indicator 25 upon a detection by the module of condition(s) indicating a likely operational failure in the near future of subsystem(s) 21 and controller 23. Examples of such conditions include, but are not limited to, (1) a premature degradation of the operational component(s) 22 of subsystem(s) 21;

(2) a repeated occurrence of error conditions of the operational component(s) 22 of subsystem(s) 21 (particularly recoverable error conditions); and (3) a shortened reliable life of the operational component(s) 22 of subsystem(s) 21.

In practice, failure warning indicator 25 may also have various structures including, but not limited to:

(1) a visible light form (e.g., a green check mark for operational readiness, a red X for inoperable readiness or a flashing light for immediate attention);

(2) an iconic and/or textual visual form (e.g., an icon and/or text displayed on a monitor); and/or (3) an audio form (e.g. a series of beeps for immediate attention or a voice recording stating either operational readiness or inoperable readiness).

For example, referring to FIG. 3, a failure warning state diagram consists of self-testing/analysis state S10 (FIG. 1), subsystem monitoring state S11 (FIG. 1), error analysis state S12 (FIG. 1) and a novel and unique predictive failure analysis state S14.

As previously described herein, self-testing/analysis state S10 involves an execution of various self-testing by the emergency medical device of each subsystem of the emergency medical device.

Controller 23 is triggered to transition T7 to predictive failure analysis state S14 upon full execution of the self-tests whereby the test results are analyzed for any indication of a premature degradation of operational component(s) 22 and any error conditions are analyzed for repeated occurrences of a particular error condition or related error conditions.

Premature Degradation. The automated self-tests are typically designed with hard-failure limits to determine the pass/fail results of the test. However, not every failure mode easily falls into buckets of good or bad, because there will be instances where components will degrade over the product lifetime and will slowly pass through the pass/fail boundary of the ready-for-use tests. The present invention recognizes that for some types of self-tests, soft-failure limits may be used as predictors of future failures whereby test results outside the hard-failure limits would continue to result in failed test result and whereby test results outside the soft-failure limits but inside the hard-failure limits would result in early failure warnings.

Figure 4:
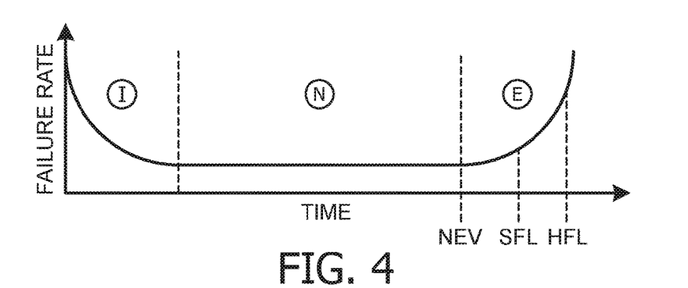
FIG. 4 illustrates an exemplary bathtub curve to demonstrate the inventive principles of a predictive failure analysis by emergency medical device in accordance with the present invention.

More particularly, referring to a "Bathtub Curve" as shown in FIG. 4, a typical lifecycle of many types of operational components 22 has three (3) distinct periods including an infant mortality I, a normal life N and end of life E. To mitigate the infant mortality failure period I, subsystems 21 may be "burned in" and/or operational components 22 are screened during manufacturing. Accordingly, a device design target is for a normal life N of each operational component 22 to extend further than the expected life of the overall device 20. However, there are many factors that may lead to premature failure of an operational component 22.

For example, a popular technology for defibrillator capacitors includes the use of metalized dry-film polypropylene energy storage capacitors. These capacitors exhibit a self-healing property where small defects in the film are removed by clearing away the affected foil area. In a high-pulse application, such as defibrillation, the mechanical and thermal stresses of normal use will occasionally create new fault sites, which will also be cleared. This results in a very small gradual decrease in capacitor value. By design, these decreases are so small that over the product lifetime, capacitors are expected to remain within rated tolerance. It is possible however that some capacitors which are subjected to conditions of extreme use, or extreme environmental conditions, may exhibit a capacitance loss which is sufficient to exceed the hard-failure limits ("HFL") of the device self-tests.

Still referring to FIG. 4, exceeding a hard-failure limit ("HFL") would create an indication that device 20 is not ready-for-use. In contrast, as exemplarily shown, a soft-failure limit ("SFL") set above the hard-failure limit ("HFL") and below a nominal expected variance ("NVE") in terms of life expectancy of an operational component 22 provides an indication that device 20 is still ready-for-use, but should be serviced soon if operational component(s) 22 are outside the soft-failure limit.

Error Condition(s). During device self-test, error conditions might be detected that are not serious enough to be considered as device failures. Examples of such errors are intermittent and recoverable error conditions. Specifically, intermittent errors might be caused by electro-magnetic interference from random noise, cosmic rays or other nearby electronic equipment. Recoverable errors might include software error conditions that can be cleared by rebooting, or data transmission errors where retransmission is possible.

When device 20 recovers from an error condition, controller 23 will continue to show device 20 is ready-for-use via indicator 24. However, if many instances of a specific recoverable error condition are observed over a short period of time, the likelihood increases that the root cause of the error is a real device failure or a latent design defect. Additionally, device performance may be impacted if the rate of occurrence of recoverable errors conditions increases.

The repeated occurrence of a particular error condition or related error conditions is therefore analyzed for any indication of a pending device failure.

Referring back to FIG. 3, if device 20 is ready-for-use, controller 23 is triggered to transition T8 to monitoring/analysis states S11/S12 upon determining a failure warning status derived from the analysis of a premature degradation of operational component(s) 22 and any repeated occurrences of error condition(s). The failure warning status is a generation or a non-generation of failure warning indicator 25.

During a normal operation of device, 20, controller 23 is periodically triggered to transition T9 back to predicative failure analysis state S14 for analyzing new or additional occurrence(s) of error condition(s) and usage patterns of specific individual component(s) 22.

Error Condition(s). During normal operation of device 20, error conditions might be detected that are not serious enough to be considered as device failures, particularly recoverable error conditions. Again, any repeated occurrence of a particular error condition or related error conditions is therefore analyzed for any indication of a pending device failure.

Component Usage. Most electrical, mechanical and electro-mechanical components 22 are subjected to wear that might shorten their useful life. For example, connectors are designed to withstand a finite number of connect/disconnect cycles whereby each connect/disconnect cycle may cause a small amount of friction wear on contact surfaces eventually wearing off gold plating needed for good electrical contact. The connectors that would be employed are rated for the expected usage. However, in extreme usage conditions, they could fail.

The usage pattern of some or all operational component(s) 22 are analyzed to ascertain if the useful life of such component(s) has been shortened.

Referring back to FIG. 3, controller 23 is again triggered to transition T8 to monitoring/analysis states S11/S12 upon determining a failure warning status derived from the analysis of any repeated occurrences of error condition(s) and of component usage patterns. Again, the failure warning status is a generation or a non-generation of failure warning indicator 25.

Also during the normal operation of device 20, controller 23 may be triggered to transition T10 back to self-testing/analysis state S10 upon re-initiation of device 20 to overcome a non-recoverable error or failure of device 20. As previously described herein, if device 20 is ready-for-use, the test results are again analyzed for any indication of a premature degradation of operational component(s) 22 and any test error conditions are again analyzed for repeated occurrences of any particular error condition or related error conditions.

Referring back to FIG. 2, in practice, the failure warning state diagram of FIG. 3 may be implemented in various modes by a controller 23, but regardless the subject state diagram detects condition(s) that indicate a subsystem 21 of the emergency medical device 20 is likely to operationally fail in the near future.

Figure 5:
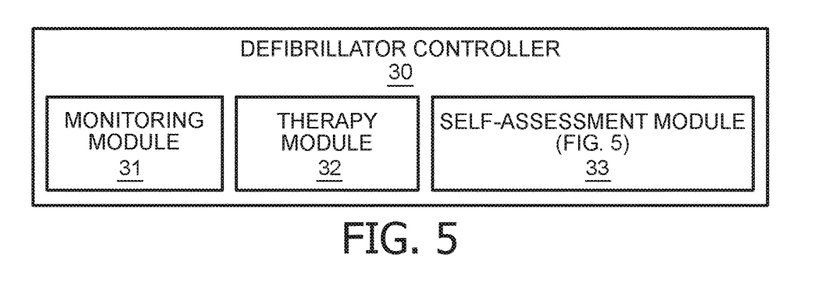
FIG. 5 illustrates an exemplary embodiment of a defibrillator controller in accordance with the present invention.

To facilitate a further understanding of a predicative failure analysis of the present invention, FIG. 5 illustrates an exemplary defibrillator controller 30 employing a monitoring module 31 for controlling an activation of an ECG module subsystem and a therapy module 32 for controlling an activation of a defibrillation therapy subsystem.

Figure 6:
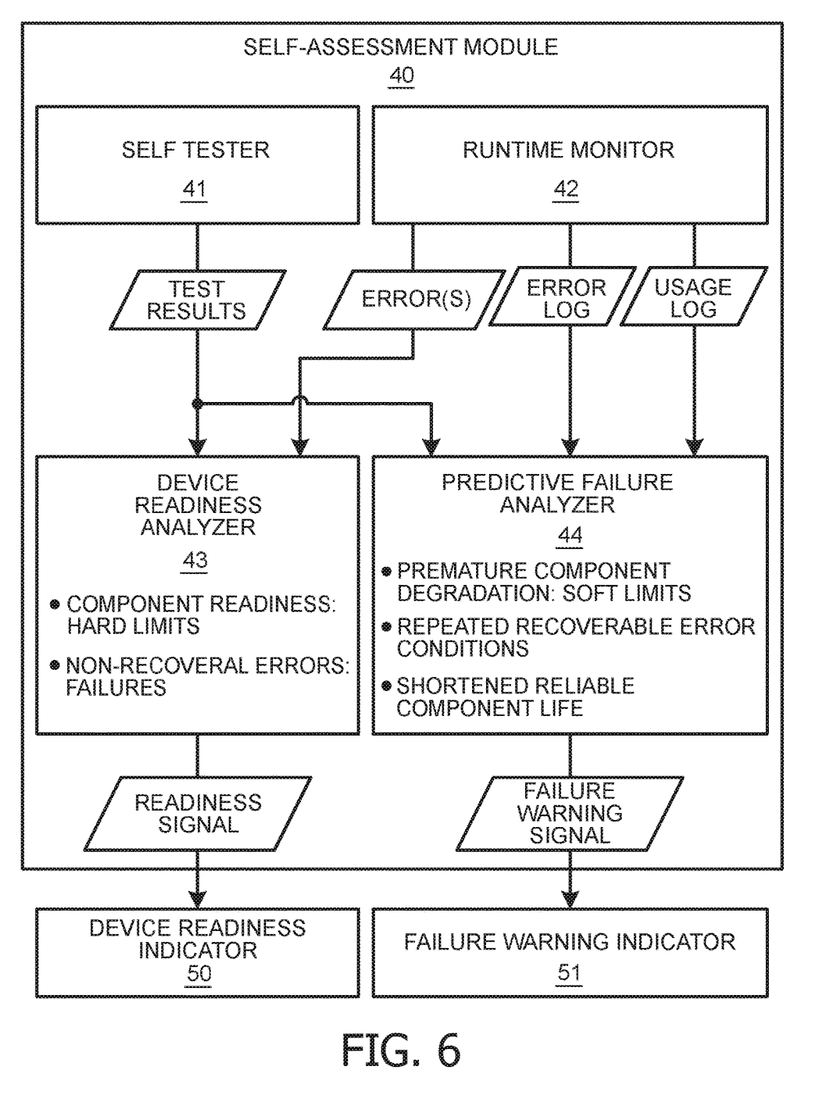
FIG. 6 illustrates an exemplary embodiment of a readiness module in accordance with the present invention.

Defibrillation controller 30 further employs a self-assessment module 33 for executing self-testing and predictive failure analysis of the subsystems. In practice, self-assessment module 33 may consist of sub-modules for separately executing the self-testing and predictive failure analysis of the subsystems, or may be a single module for integrally executing the self-testing and predictive failure analysis of the subsystems. FIG. 6 illustrates an embodiment 40 of self-assessment module 33 integrally executing the self-testing and predictive failure analysis of the subsystems.

Referring to FIG. 6, self-assessment module 40 employs a self-tester 41, a runtime monitor 42, a device readiness analyzer 43 and a predicative failure analyzer 44. Module 40 will described based on data flow between components 41-44.

Self-tester 41 executes known self-tests to ensure all subsystems are functioning properly. These self-tests are automatically initiated periodically when the device has power but is turned off (e.g., not in clinical use). The self-test produces pass/fail results inclusive of any occurrence of recoverable error condition(s) that are communicated to analyzers 43 and 44 directly or via storage retrieval.

Runtime monitor 42 monitors the device for any occurrence of an error condition, particularly a failure, as the device is turned on (e.g., in clinical use). Upon detection of an error condition, runtime error monitor 42 will initiate steps necessary to attempt a recovery of the error condition, and logs the condition(s) and recovery effort(s). An error condition is communicated to device readiness analyzer 43 directly or via storage retrieval, and the error log is communicated to predicative failure analyzer 44 directly or via storage retrieval.

Runtime monitor 42 further generates a usage log informative of various component usage patterns including, but not limited to:

(1) a counting of a number of charge cycles of the defibrillator's therapy capacitor;

(2) a counting of a number of charge/discharge cycles on the defibrillator's batteries;

(3) a counting of a number of on/off cycles of switches;

(4) a counting of a number of open/close cycles of relays;

(5) a counting of a number of connect/disconnect cycles of external connector ports;

(6) logging exposure to extreme temperatures that can overstress solder bonds, or crack semiconductor dies and packaging (e.g. using an internal thermistor);

(7) logging exposure to extreme humidity that can cause corrosion or cracking (e.g. using an internal hygrometer); and (8) logging exposure to extreme shock and vibration conditions that can accelerate degradation of components such as electrical contacts of connectors.

Runtime monitor 42 communicates the usage log to predictive failure analyzer 45 directly or via storage retrieval.

Device readiness analyzer 43 analyzes the test results against hard failure limits and analyzes the errors to ascertain as known in the art if the device is ready-for-use or has a failure that requires immediate servicing, and applies a readiness signal to a device readiness indicator 50 (e.g., a light, a speaker, etc.) to actuate/energize indicator 50 in indicating the device is operationally ready for clinical use or inoperable for clinical use and is need of immediate service.

In response to the test results, predictive failure analyzer 44 ascertains whether any components are showing a premature degradation. To this end, analyzer 44 applies soft-functional limits to the components including, but not limited to:

(1) power subsystem voltage level tests;

(2) timing of components with optical detectors subject to occlusion wear;

(3) capacitance of the defibrillator's therapy capacitor(s); and (4) charge capacity of the defibrillator's battery In response to testing errors and error logs, predictive failure analyzer 44 ascertains whether a repeated occurrence of a specific error condition or related error conditions warrants a warning of a pending subsystem failure.

More particularly, single occurrences of a recoverable error condition where a threshold of multiple sequential occurrences of such error condition would render the device unusable warrants a warning of a pending subsystem failure.

Additionally, single occurrences of a non-recoverable error (failure) condition that is cleared by successful self-tests may warrant a warning of a pending subsystem failure. For example, when each failure occurs, analyzer 43 will ascertain the device is not-ready-for-use. However, the defibrillator user might initiate self-tester 41 and the failure may not reoccur, causing analyzer 43 to change indicator 50 to ready-for-use. If such an intermittent failure condition reoccurs too frequently as measured against a threshold, it indicates an increase in the likelihood of an impending hard failure and warrants a warning of a pending subsystem failure.

In response to the usage logs, analyzer 44 will measure the usage patterns against thresholds representative of an unacceptable shortening of a reliable useful life of the operational components.

From the various predicative failure tests, analyzer 45 will generate a failure warning signal to energize or actuate a failure warning indicator 51 (e.g., a light, a speaker, etc.) upon a detection of a likely failure in the operational readiness in the near future of operational components/subsystems of the defibrillator.

Referring to FIGS. 2-6, those having ordinary skill in the art will appreciate numerous benefits of the present including, but not limited to:

(1) A reduction in a the likelihood that a defibrillator or other emergency use medical device will fail when it is needed for clinical use. Particularly, a device user gets a warning, in advance, if the device detects conditions that indicate that an internal component or subsystem is likely to fail in the near future. This warning allows the device user to repair or replace the device before it is needed for an emergency;

(2) A reduction in device maintenance and service costs. Particularly, with current ready-for-use technologies, in many cases a device will be returned to the factory due to a failure indication but the problem cannot be reproduced. The most likely component (i.e. a circuit board) will be replaced, and the device is returned to the customer. This process may repeat multiple times before other components, for example the therapy capacitor, will finally be replaced resolving the problem. By predicative failure analysis of the present invention, number of false failures is reduced because failure trends are indicated differently than hard-failures. Additionally, the predicative failure analysis provides specific diagnostic information such as trending data for the component nearing failure and (3) A reduction in a cost of ownership for the device. Particularly, some device components might have shorter expected lifetimes than the device itself. Examples are batteries and accessories such as patient vital signs sensors and cables. With current practices, the users are instructed by the manufacturer to replace these components on a schedule established by reliability life analysis and testing. In other words, the battery might need to be replaced every three years based on expected device usage scenarios. By predicative failure analysis of the present invention, device usage conditions are logged whereby a battery in a lightly-used device may be replaced less frequently.

Furthermore, as one having ordinary skill in the art will appreciate in view of the teachings provided herein, features, elements, components, etc. described in the present disclosure/specification and/or depicted in the FIGS. 2-6 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 2-6 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive advance warning indicators for emergency medical devices, (which embodiments are intended to be illustrative and not limiting), it is noted that modifications and variations can be made by persons having ordinary skill in the art in light of the teachings provided herein, including the FIGS. 2-6. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An emergency medical device, comprising:
   an emergency medical subsystem including at least one operational component operable to execute an emergency medical procedure; and
   an emergency medical controller operable to control an activation of the emergency medical subsystem,
      wherein the emergency medical controller is structurally configured to conditionally actuate a device readiness indicator indicative of an operational readiness of the at least one operational component to execute the emergency medical procedure, and
      wherein the emergency medical controller is structurally configured to conditionally actuate a failure warning indicator indicative of a pending failure of the operational readiness of the at least one operational component to execute the emergency medical procedure as indicated by the device readiness indicator.

2. The emergency medical device of claim 1,
   wherein the emergency medical controller is structurally configured to conduct an operational readiness test of the at least one operational component;
   wherein the emergency medical controller actuates the device readiness indicator responsive to a pass result of the operational readiness test; and
   wherein the emergency medical controller actuates the failure warning indicator responsive to the pass result of the operational readiness test indicating a premature degradation of the at least one operational component.

3. The emergency medical device of claim 1,
   wherein the emergency medical controller is structurally configured to log repeated occurrences of an error condition of the at least one operational component; and
   wherein the emergency medical controller actuates the failure warning indicator responsive to a warning frequency of the repeated occurrences of the error condition of the at least one component.

4. The emergency medical device of claim 3, wherein the error condition is recoverable by the emergency medical controller.

5. The emergency medical device of claim 3, wherein the error condition is non-recoverable by the emergency medical controller.

6. The emergency medical device of claim 1,
   wherein the emergency medical controller is structurally configured to monitor a usage pattern of the at least one operational component; and
   wherein the emergency medical controller actuates the failure warning indicator responsive to the usage pattern indicating a shortened reliable life of the at least one operational component.

7. The emergency medical device of claim 1, wherein the device readiness indicator and the failure warning indicator are integrated indicators.

8. The emergency medical device of claim 1, wherein the device readiness indicator and the failure warning indicator are segregated indicators.

9. The emergency medical device of claim 1, wherein the emergency medical controller includes:
   a predictive failure analyzer structurally configured to actuate the failure warning indicator based on at least one of a predictive failure analysis of a premature degradation of the at least one operational component, a repeated occurrence of error conditions of the at least one operational component and a shortened reliable life of the at least one operational component.

10. An emergency medical device, comprising:
    an emergency medical subsystem including at least one operational component structurally configured to execute an emergency medical procedure; and
    an emergency medical controller structurally configured to control an activation of the emergency medical subsystem,
       wherein the emergency medical controller is structurally configured to conditionally actuate a failure warning indicator indicative of a pending failure of the operational readiness of the at least one operational component to execute the emergency medical procedure.

11. The emergency medical device of claim 10,
    wherein the emergency medical controller is structurally configured to conduct an operational readiness test of the at least one operational component; and
    wherein the emergency medical controller actuates the failure warning indicator responsive to a pass result of the operational readiness test indicating a premature degradation of the at least one operational component.

12. The emergency medical device of claim 10,
    wherein the emergency medical controller is structurally configured to log repeated occurrences of an error condition of the at least one operational component; and
    wherein the emergency medical controller actuates the failure warning indicator responsive to a warning frequency of the repeated occurrences of the error condition of the at least one component.

13. The emergency medical device of claim 12, wherein the error condition is recoverable by the emergency medical controller.

14. The emergency medical device of claim 12, wherein the error condition is non-recoverable by the emergency medical controller.

15. The emergency medical device of claim 10,
wherein the emergency medical controller is structurally configured to monitor a usage pattern of the at least one operational component; and
wherein the emergency medical controller actuates the failure warning indicator responsive to the usage pattern indicating a shortened reliable life of the at least one operational component.

16. A method of operating an emergency medical device including an emergency medical controller and at least one operational component, the method comprising:
conditionally generating, by the emergency medical controller, a device readiness indicator indicative of an operational readiness of the at least one operational component to execute an emergency medical procedure; and
conditionally generating, by the emergency medical controller a failure warning indicator indicative of a pending failure of the operational readiness of the at least one operational component as indicated by the device readiness indicator.

17. The method of claim 16,
wherein the conditionally generating the device readiness indicator by the emergency medical controller includes the emergency medical controller:
conducting an operational readiness test of the at least one operational component; and
actuating the device readiness indicator responsive to a pass result of the operational readiness test; and
wherein the conditionally generating the failure warning indicator by the emergency medical controller includes the emergency medical controller:
actuating the failure warning indicator responsive to the pass result of the operational readiness test indicating a premature degradation of the at least one operational component.

18. The method of claim 16,
wherein the conditionally generating the failure warning indicator by the emergency medical indicator includes the emergency medical controller:
logging repeated occurrences of an error condition of the at least one operational component; and
actuating the failure warning indicator responsive to a warning frequency of the repeated occurrences of the error condition of the at least one component.

19. The method of claim 18, wherein the error condition is recoverable by the emergency medical controller.

20. The method of claim 18, wherein the error condition is non-recoverable by the emergency medical controller.

21. The method of claim 16,
wherein the conditionally generating the failure warning indicator by the emergency medical controller includes the emergency medical controller:
responsive to a generation of the device readiness indicator, monitoring a usage pattern of the at least one operational component; and
actuating the failure warning indicator responsive to the usage pattern indicating a shortened reliable life of the at least one operational component.

\* \* \* \* \*